US 6,821,013 B2

(12) United States Patent
Reilly et al.

(10) Patent No.: US 6,821,013 B2
(45) Date of Patent: Nov. 23, 2004

(54) ADAPTERS, ADAPTER SYSTEMS AND METHOD FOR USE IN CONNECTION WITH POWERED INJECTORS FOR AGITATION OF MULTI-COMPONENT FLUIDS

(75) Inventors: David M. Reilly, Glenshaw, PA (US); David M. Griffiths, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 167 days.

(21) Appl. No.: 10/316,379

(22) Filed: Dec. 11, 2002

(65) Prior Publication Data

US 2003/0117888 A1 Jun. 26, 2003

Related U.S. Application Data

(60) Provisional application No. 60/343,075, filed on Dec. 20, 2002.

(51) Int. Cl.$^7$ .......................... B01F 15/00; B01F 15/02; B01F 15/04
(52) U.S. Cl. .................... 366/162.3; 366/189; 366/190; 222/286; 604/131
(58) Field of Search ............................. 366/162.3, 189, 366/190; 222/386; 604/416, 131

(56) References Cited

U.S. PATENT DOCUMENTS

| | | |
|---|---|---|
| 4,322,022 A | 3/1982 | Bergman |
| 4,934,827 A | 6/1990 | Taschke et al. |
| 5,286,105 A | 2/1994 | Herold et al. |
| 5,383,858 A | 1/1995 | Reilly et al. |
| 5,808,203 A | 9/1998 | Nolan, Jr. et al. |
| 5,860,739 A | 1/1999 | Cannon |
| 5,944,694 A | 8/1999 | Hitchins et al. |
| 6,315,164 B1 | 11/2001 | Muhlbauer et al. |
| 6,317,623 B1 | 11/2001 | Griffiths et al. |
| 6,397,098 B1 | 5/2002 | Uber, III et al. |
| 6,575,930 B1 | 6/2003 | Trombley, III et al. |
| 6,673,033 B1 | 1/2004 | Sciulli et al. |

FOREIGN PATENT DOCUMENTS

| | | |
|---|---|---|
| WO | WO 99/27981 | 6/1999 |
| WO | WO 00/53242 | 9/2000 |
| WO | WO 01/37903 | 5/2001 |

OTHER PUBLICATIONS

International Search Report for Counterpart PCT Application No.: PCT/US02/39653.

*Primary Examiner*—Tony G. Soohoo
(74) *Attorney, Agent, or Firm*—Gregory L. Bradley; Henry E. Bartony, Jr.

(57) ABSTRACT

An adapter for use with a powered injector imparts agitating motion to a syringe, which is connectable to the powered injector. The powered injector includes a drive member to impart motion to a plunger slidably disposed within the syringe. The adapter includes an injector attachment mechanism to attach the adapter to the powered injector and a syringe interface to attach the syringe to the adapter. The adapter preferably further includes an intermediate drive member having a drive attachment to attach the intermediate drive member to the drive member of the powered injector and a plunger attachment member to attach the intermediate drive member to the syringe plunger. The intermediate drive member is operable to translate motion of the drive member of the powered injector to the syringe plunger. The adapter also includes at least one powered agitator to provide agitating motion the syringe interface.

17 Claims, 10 Drawing Sheets

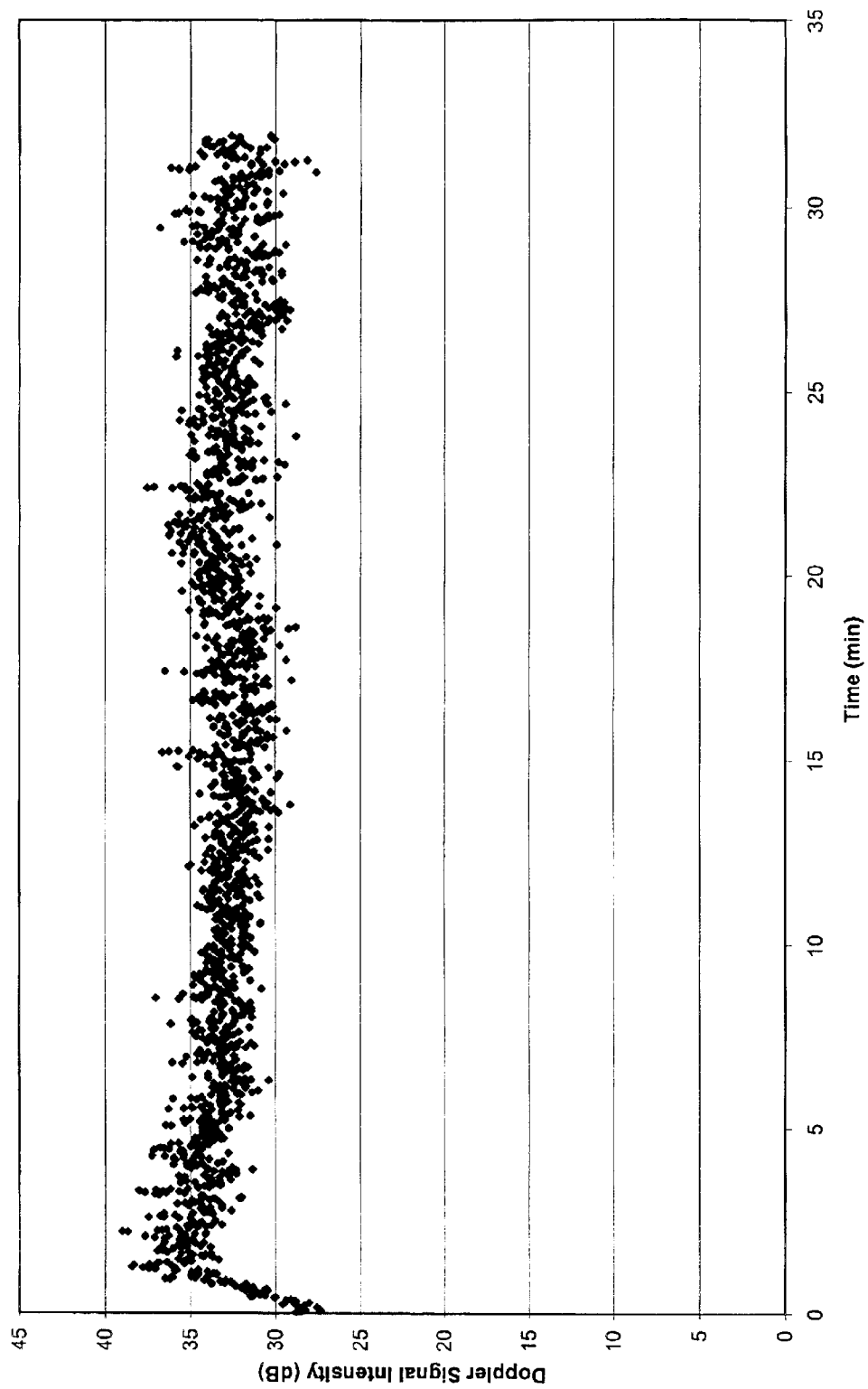

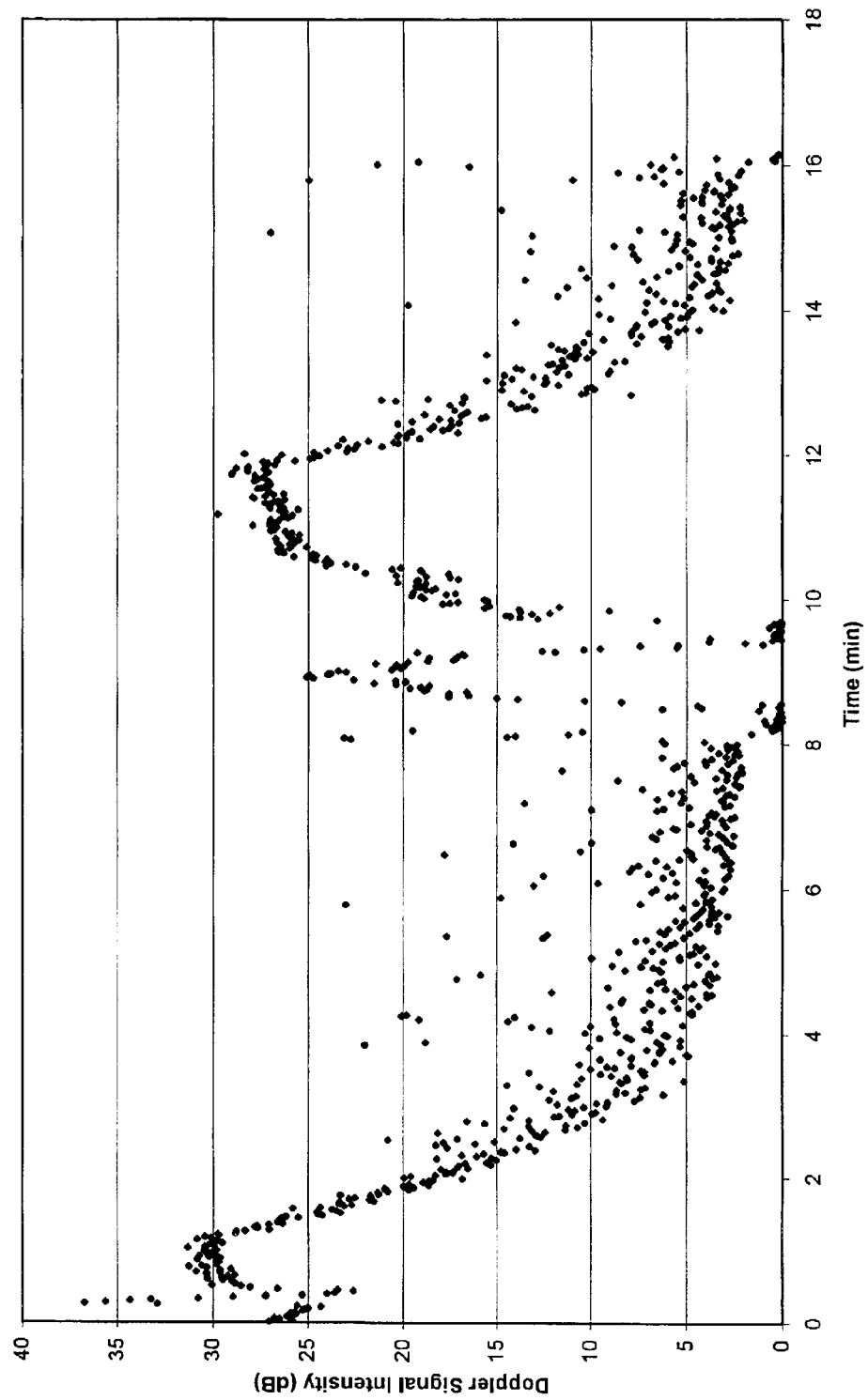

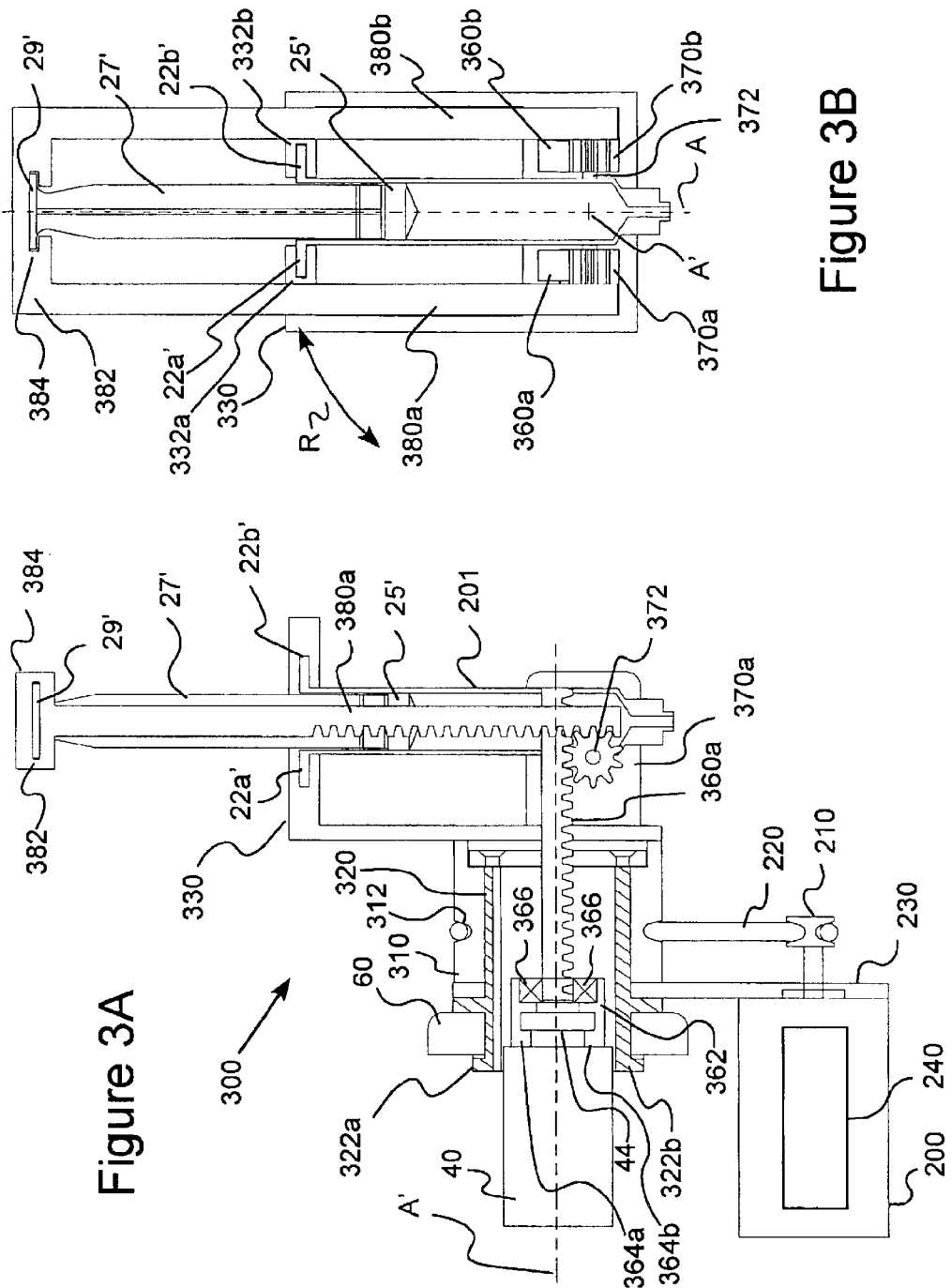

ADAPTERS, ADAPTER SYSTEMS AND METHOD FOR USE IN CONNECTION WITH POWERED INJECTORS FOR AGITATION OF MULTI-COMPONENT FLUIDS

CROSS REFERENCE TO RELATED APPLICATION

This application claims the benefit of U.S. Provisional Application Ser. No. 60/343,075, filed on Dec. 20, 2001, the contents of which are incorporated herein by reference.

BACKGROUND OF THE INVENTION

The present invention relates generally to creation and maintenance of multi-component fluids, and, especially, to adapters, adapter systems and methods of using adapters in connection with powered injectors for agitation of multi-component injection fluids.

In a number of medical procedures, it is desirable to inject a multi-component injection medium into a patient. An example of such a medical procedure is ultrasound imaging.

Ultrasound imaging creates images of the inside of the human body by broadcasting ultrasonic energy into the body and analyzing the reflected ultrasound energy. Differences in reflected energy (for example amplitude or frequency) appear as differences in gray scale or color on the output images. As with other medical imaging procedures, contrast-enhancing fluids (often referred to as contrast media) can be injected into the body to increase the difference in the reflected energy and thereby increase the contrast in the image viewed by the operator.

For ultrasonic imaging, the most common contrast media contain many small bubbles. The difference in density of bubbles when compared to water, and thus their difference in sound transmission, makes small gas bubbles excellent means for scattering ultrasound energy. Small solid particles can also serve to scatter ultrasonic energy. Such particles are typically on the order of 1 to 10 microns (that is, $10^{-6}$ to $10^{-5}$ meters) in diameter. These small particles can pass safely through the vascular bed.

Contrast media suitable for use in ultrasound are supplied in a number of forms. Some of these contrast media are powders to which liquid is added just before use. The powder particles cause a gas bubble to coalesce around them. The powder must be mixed with a liquid, and the mixture must be agitated with just the right amount of vigor to get the optimum creation of bubbles. Another type of contrast medium is a liquid that is agitated vigorously with air. There are no solid particles to act as nuclei, but the liquid is a mixture of several liquid components that make relatively stable small bubbles. A third type of contrast medium uses "hard" spheres filled with a gas. These contrast media are typically supplied as a powder that is mixed with a liquid. The goal is to suspend the spheres in the liquid without breaking them. Even though such spheres have a shell that is hard compared to a liquid, they are very small and relatively fragile. It is also possible for the solid particles themselves to act to scatter ultrasonic energy, but the acoustical properties of the solid spheres are not as different from liquid as those of a gas, so the difference in reflected energy is not as strong.

After mixing/preparation as described above, the contrast medium is drawn into a syringe or other container for injection into the patient. Typically, the fluid is injected into a vein in the arm of the patient. The blood dilutes and carries the contrast medium throughout the body, including to the area of the body being imaged.

It is becoming more common for a microprocessor controlled powered injector to be used for injecting the contrast medium to maintain a consistent flow over a long time, thereby providing a consistent amount of contrast medium (number of particles) in the blood stream. If there are too few particles in a region of interest, for example, there is insufficient image contrast and the diagnosis cannot be made. If too many particles are present, too much energy is reflected, resulting in blooming or saturation of the ultrasound receiver.

Although a power injector can inject contrast medium at a constant flow rate, there must be a constant number of bubbles per volume of fluid injected to provide a constant image contrast. Because a gas is significantly less dense than water and other liquids, however, gas bubbles will rise in a liquid. The rate of rise is related to the diameter of the gas bubble. This density difference is useful to quickly separate large bubbles created during the initial mixing. However, the small bubbles desired for image enhancement will also rise slowly. Solid particles, on the other hand, tend to settle or sink because most solids are denser than water. Many minutes can elapse between the initial mixing of the contrast medium and the injection into the patient, and/or the injection itself may be several minutes in duration. Certain multi-component contrast media undergo significant separation after only a few minutes. If the concentration of particles changes over the volume of fluid, the image contrast will degrade.

The benefits of agitation of multi-component fluids to create, improve or maintain homogeneity via a number of techniques are discussed, for example, in U.S. patent application Ser. No. 09/267,237, filed Mar. 12, 1999, assigned to the assignee of the present invention, the disclosure of which is incorporated herein by reference. Likewise, Published PCT Application No. WO 99/27981 discloses powered injectors designed to agitate contrast medium to, for example, maintain suspension of media such as ultrasound bubbles and provides representative studies of the efficacy of those powered injectors.

It remains desirable to develop improved systems, devices and method to maintain multi-component contrast media in a mixed or homogeneous state throughout an injection proceeding. It is particularly desirable to develop such systems, devices and methods that are suitable for use with existing powered injectors and injector systems.

SUMMARY OF THE INVENTION

The present invention provides generally, devices, systems and methods for creating and/or agitating a multi-component medium (for example, an ultrasound contrast medium, a medicant including a suspended agent etc.) suitable for injection into a patient.

In one aspect, the present invention provides an adapter for use with a powered injector to impart agitating motion to a syringe, which is connectable to the powered injector. As used herein, the term "syringe" refers to fluid containers from which a pressurized fluid can be ejected. Often a syringe includes a generally cylindrical barrel through which a piston or plunger is movable to aspirate fluid into the syringe and to eject pressurized fluid. As used herein, the term "powered injector" refers to any powered mechanism used to pressurize the contents of a syringe. Examples of powered injectors include, but are not limited to, MEDRAD PULSAR® injectors available from Medrad, Inc. of Indianola, Pa. and Harvard Apparatus syringe pumps available from Instech Laboratories, Inc. of Plymouth Meeting, Pa. Powered injectors typically include a drive member to impart motion to a plunger slidably disposed within the syringe.

The adapter includes an injector attachment mechanism to attach the adapter to the powered injector and a syringe interface to attach the syringe to the adapter. In many cases, the injector attachment mechanism of the adapter is preferably of the same type as an attachment mechanism on the syringe that is used to attach the syringe to a syringe interface on the injector. Likewise, the syringe interface on the adapter is preferably of the same type as the syringe interface on the powered injector. The adapter preferably further includes an intermediate drive member having a drive attachment to attach the intermediate drive member to the drive member of the powered injector and a plunger attachment member to attach the intermediate drive member to the syringe plunger. The intermediate drive member is operable to translate motion of the drive member of the powered injector to the syringe plunger. The adapter also includes at least one powered agitator to provide agitating motion to the syringe interface (and thereby to the syringe attached thereto).

As used herein, the term "agitating motion" refers generally to motion other than the reciprocal sliding motion of the syringe plunger and can, for example, include any number of types of motions suitable to cause mixing of fluid components within the syringe including, but not limited to, rotational motion, orbital motion and/or vibrational motion. In one embodiment, the adapter rotates the syringe interface to rotate the syringe about its longitudinal axis. The adapter can also or alternatively rotate the syringe interface to rotate the syringe about an axis perpendicular to its longitudinal axis. Likewise, the adapter can also or alternatively orbit the syringe interface about an orbital axis to orbit the syringe about the orbital axis.

The intermediate drive member can, for example, include a rigid and/or a flexible connector to facilitate agitating motion.

In one embodiment, the adapter includes a first hydraulic cylinder to which the injector attachment mechanism is connected. The first hydraulic cylinder is in fluid connection via at least one flexible line with a second hydraulic cylinder to which the syringe interface is connected.

In another embodiment, the adapter includes a motor and a drive belt in operative connection with the syringe interface. The motor can, for example, rotate the syringe interface via the drive belt to impart rotation of the syringe about its longitudinal axis, to impart rotation of the syringe about an axis generally perpendicular to its longitudinal axis or to impart orbital motion to the syringe. In one embodiment in which orbital motion is imparted to the syringe, the adapter includes a first section to which the injector attachment mechanism is connected and a second section to which the syringe interface is connected. The second section is connected to the first section at an angle so that the syringe interface orbits about an axis when the first section is rotate. The drive belt is preferably in operative connection with the first section to rotate the first section about its longitudinal axis.

In another aspect, the present invention provides a powered injector system including a powered injector having a drive member to impart motion to a syringe plunger slidably disposed in a syringe that is connectable to the powered injector and an adapter as described above to impart agitating motion to the syringe.

In still another aspect, the present invention provides a method of providing a powered injector or powered injector system with the capability to impart the agitating motion to a syringe, which is connectable to the powered injector. The method includes the step of: attaching an adapter as described above to the powered injector. The method preferably also includes the steps of attaching a syringe to the syringe interface and activating the powered agitator. The method can also include the step of sensing the syringe configuration of a syringe attached to the syringe interface. The powered agitator can, for example, be controlled in correspondence with the sensed syringe configuration. Likewise, the control of the injection via control of the powered injector drive member can be controlled in a manner consistent with sensed syringe configuration.

Unlike currently available agitation devices, systems and methods for agitating multi-component injection fluids, the adapters, systems and methods of the present invention do not require specific, dedicated and/or redesigned powered injectors. To the contrary, the adapters, systems and methods of the present invention can be used with virtually any currently available powered injector to add the capability to that injector to impart agitating motion to a syringe. The adapters, systems and methods of the present invention thereby provide a substantial improvement in the art. For example, operating personnel can continue to use existing powered injectors with which they have become acquainted, increasing operator efficiency and safety of operation as compared to deployment of a new injectors or injector systems. Moreover, the adapters of the present invention can provide cost savings as compared to deployment of new injectors or injector systems.

BRIEF DESCRIPTION OF THE DRAWINGS

FIG. 2C illustrates graphically experimental data of the effect of agitation of LEVOVIST ultrasound contrast on signal intensity as a function of time using the adapter of FIG. 2A.

FIG. 2D illustrates graphically experimental data of image intensity as a function of time for LEVOVIST ultrasound contrast medium injected without agitation.

FIG. 3A illustrates a side cross-sectional view of another embodiment of an adapter of the present invention for use in connection with a powered injector in which the syringe is rotated about an axis transverse to the longitudinal axis of the syringe.

FIG. 3B illustrates a front view of a portion of the adapter of FIG. 2A.

DETAILED DESCRIPTION OF THE INVENTION

In several embodiments, the present invention provides devices, systems and methods to facilitate or to improve the initial creation and/or mixing of a multi-component injection fluid such as an ultrasound contrast medium and to agitate the contrast medium to maintain a relatively uniform distribution of the contrast enhancing agent or particles throughout the liquid contrast medium prior to and/or during an injection procedure. The present invention is, additionally, applicable generally to multi-component fluids wherein the fluid components are not totally miscible and there is a tendency for the components to separate over time (for example, because of differences in density). The present invention is also applicable to miscible or dissolvable materials during the initial preparation phase when a uniform mixture has not yet been created.

Figure 1:
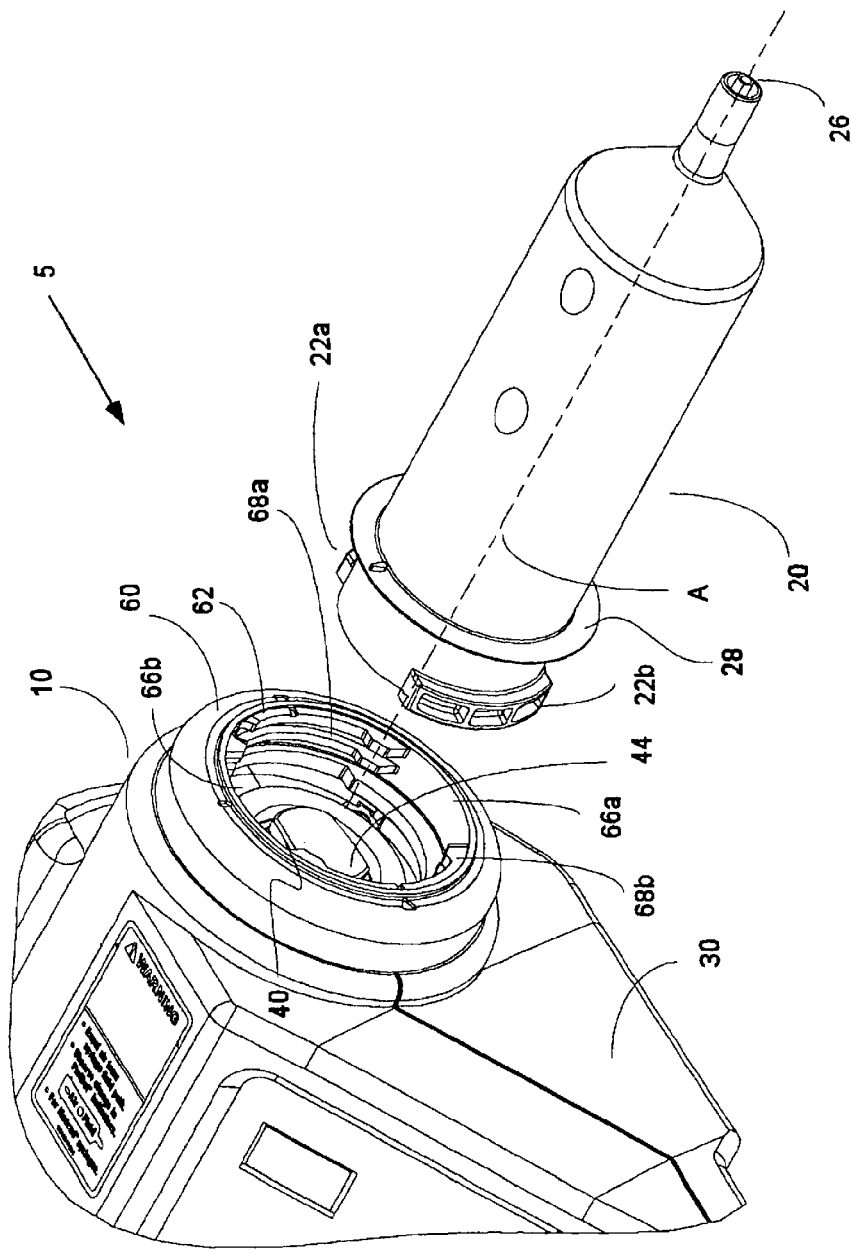
FIG. 1 illustrates a front perspective view of an injector system with which several representative embodiments of the adapters of the present invention cooperate to agitate an injection medium.

In general, the present invention provides adapters that cooperate with a powered injector in a manner such that the motion of the drive member of the injector to control a syringe plunger is translated to the syringe plunger, but through which additional motion, suitable to agitate to a multi-component fluid within the syringe, is imparted to the syringe. In several representative embodiments of the present invention such adapters attach to a front-loading injector system 5 as illustrated in FIG. 1. As clear to one skilled in the art, however, the adapters of the present invention are easily and readily used with a wide variety of injector types through, for example, simple modification of attachment mechanisms. For example, see U.S. Pat. Nos. 5,383,858, 5,944,694 and PCT Publication No. WO 01/37903, the disclosures of which are hereby incorporated by reference.

Injector system 5 includes a powered injector 10 and a syringe 20 for injection of, for example, a contrast medium. Injector housing 30 of injector 10 preferably includes a first drive member or piston 40 therein that cooperates with a syringe plunger slidably disposed in syringe 20 to inject a fluid from the interior of syringe 20 into a patient.

As used herein to describe, for example, injector 10 and syringe 20, the terms "axial" or "axially" refer generally to, for example, an axis such as axis A (see FIG. 1) around which syringe 20 is preferably formed (although not necessarily symmetrically therearound) and to directions collinear with or parallel to axis A. The terms "proximal" or "rearward" refer generally to an axial or a longitudinal direction toward the end of injector housing 30 opposite the end to which syringe 20 is mounted. The terms "distal" or "forward" refer generally to an axial or a longitudinal direction toward a syringe tip 26 of syringe 20 (from which pressurized fluid exits syringe 20). The term "radial" refers generally to a direction normal to an axis such as axis A.

Syringe 20 is, for example, removably connected to front-loading injector 10 as described, for example, in U.S. Pat. No. 5,383,858, the disclosure of which is incorporated herein by reference. In that regard, front-loading injector 10 can include a syringe mount or syringe interface 60 having a first opening 62 formed therein. Piston 40 is reciprocally mounted within injector 10 and is extendible through opening 62 in syringe interface 60. Piston 40 can, for example, include a piston flange or head 44 to assist in forming a connection with syringe plunger 25 (see, for example, FIG. 2). In the embodiment of FIG. 1, syringe interface 60 includes receiving slots 66a and 66b, which are positioned opposite one another around opening 62. Receiving flanges 68a and 68b are positioned opposite one another and between receiving slots 66a and 66b and extend inwardly into opening 62.

In the embodiment of FIG. 1, the rearward end of syringe 20 includes a releasable mounting mechanism such as a pair of mounting flanges 22a and 22b for mounting syringe 20 in a desired position relative to the front wall of injector 10. To attach syringe 20 to injector 10, the rearward end of syringe 20 is inserted into injector opening 62 such that mounting flanges 22a and 22b are inserted into receiving slots 66a and 66b, respectively. Piston flange 44 can, for example, engage a connection mechanism such as capture members 26a and 26b on the rear of syringe plunger 25 (illustrated, for example, in FIG. 2A) as, for example, described in U.S. Pat. No. 5,383,858. As clear to one skilled in the art, however, many types of cooperating connection mechanisms can be used to connect an injector drive member to a syringe plunger. For example, see U.S. Pat. No. 5,944,694 and PCT Publication No. WO 01/37903, the disclosures of which are hereby incorporated by reference.

Once mounting flanges 22a and 22b are inserted into receiving slots 66a and 66b, respectively, and piston 40 is in position to be received by the plunger, the operator rotates syringe 20 approximately 90 degrees such that mounting flanges 22a and 22b move behind and are engaged by receiving flanges 68a and 68b, respectively. Injector 10 may include a stop mechanism (not shown), for example, extending from at least one of the retaining slots 68a and 68b, to prevent rotation of syringe 20 more than 90 degrees. A sealing flange 28 on the rear of syringe 20 forward of flanges 22a and 22b prevents injection fluid from the exterior of syringe 20 from entering injector 10. Sealing flange 28 also assists in ensuring secure connection of syringe 20 to injector 10 and in positioning syringe 20 on injector 10 in a predetermined axial position relative to injector 10. Tactile, visual or audible feedback can be provided to the operator via, for example, cooperating members on syringe 20 (for example, on sealing flange 28) and injector 10 to inform the operator that secure connection has been achieved. After securely attaching syringe 20 to injector 10, advancing piston 40 in a forward direction will apply a motive force to plunger 25 to advance the plunger forward within syringe 20, thereby forcing the contents of syringe 20 out of syringe tip 26 into the fluid path to the patient. Retracting piston 40 in a rearward direction will cause the plunger to move rearward within syringe 20, thereby drawing fluid into syringe 20.

Figure 2A:
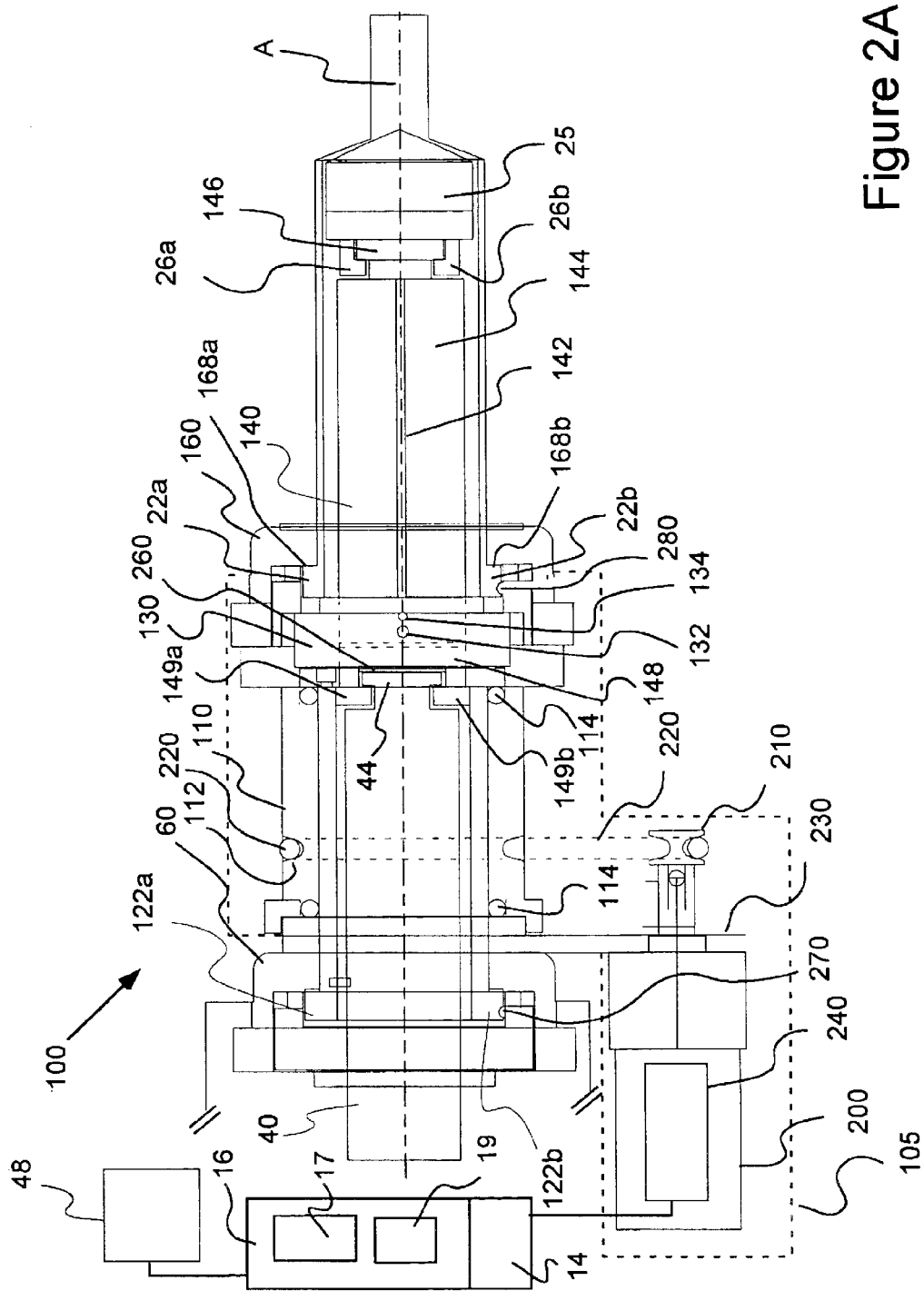
FIG. 2A illustrates a cutaway view of one embodiment of an adapter of the present invention for use in connection with a powered injector in which the syringe (illustrated as transparent) is rotated about its longitudinal axis.
Figure 2B:
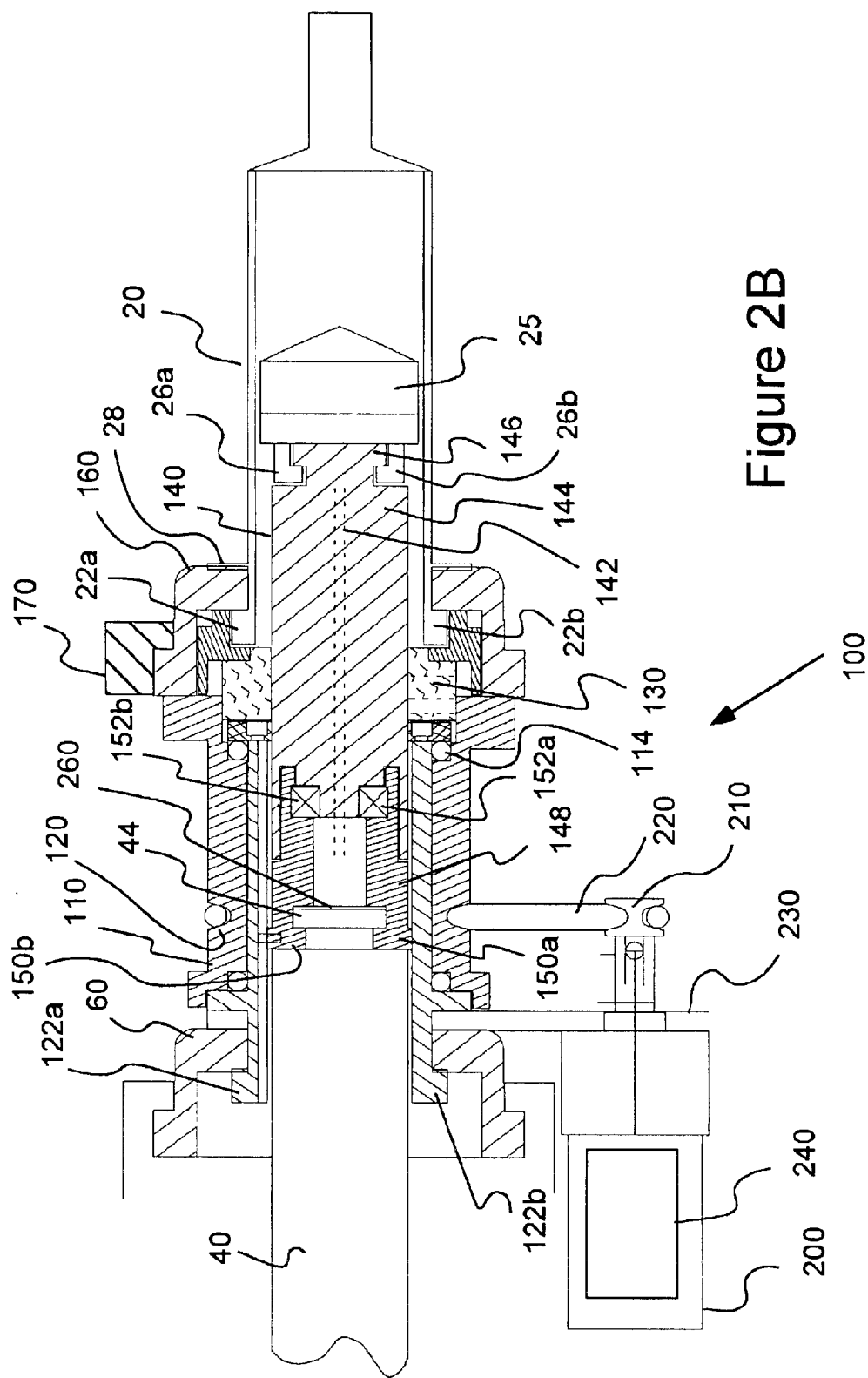
FIG. 2B illustrates a cross-sectional view of the adapter of FIG. 2A.

In the embodiment of FIGS. 2A and 2B, an adapter 100 includes an attachment mechanism for attaching to powered injector 10. The attachment mechanism of the embodiment of FIGS. 2A and 2B includes two flanges 122a and 122b that cooperate with receiving slots 66a and 66b and receiving flanges 68a and 68b of syringe interface 60 as described above for syringe flanges 22a and 22b to removably attach adapter 100 to injector 10. As clear to one skilled in the art however, many attachment mechanisms are suitable for use in the adapters of the present invention for attachment to or cooperation with virtually any type of powered injector. Adapter 100 further includes an intermediate drive member, such as a piston extension 140, that attaches to piston 40 of injector 10 to removably and operatively connect piston extension 140 to piston 40. Forward motion of piston 40 thus results in forward motion of piston extension 140, and rearward motion of piston 40 results in rearward motion of piston extension 140. Adapter 100 also includes a syringe interface 160 that includes receiving slots (not shown, but operatively equivalent to receiving slots 66a and 66b) and receiving flanges 168a and 168b that operate as described above for receiving slots 66a and 66b and receiving flanges 68a and 68b of injector 10 to removably attach syringe 20 to adapter 100.

In general, the adapters of the present invention preferably include an injector attachment mechanism of the type found on a particular syringe to attach the adapter to a corresponding injector. Likewise, the adapters preferably include a syringe interface similar in type to the syringe interface found on the injector to enable attachment of the corresponding syringe type to the adapter.

In the embodiment of FIGS. 2A and 2B, adapter 100 includes a power source such as a motor 200 that is operable to rotate syringe 20 about its longitudinal axis A. For example, motor 200 can rotate a pulley wheel 210 and thereby a belt 220 that is seated in a groove 112 of an exterior, rotating adapter section 110 of adapter 100 to rotate adapter section 110 about axis A. Adapter section 110 can, for example, rotate about an inner adapter section 120 of adapter 100 via bearings 114. Syringe interface 160 rotates with adapter section 110, causing syringe 20 to rotate about axis A. For example, a bushing 130 can be in operative connection with adapter section 110 (for example, via a pin member 132) and in operative connection with piston extension 140 via a pin member 134 which seats in a slot 142 in a forward, rotating section 144 of piston extension 140. Forward section 144 includes a flange 146 to connect to plunger 25 via capture members 26a and 26b as described above (in connection with piston flange 44). Bushing 130 causes forward section 144 and plunger 25 to rotate in unison or with the same direction and angular velocity as adapter section 110 and syringe 20. Plunger extension 140 also preferably includes a rear section 148 that does not rotate. Rear section 148 includes capture members 149a and 149b (similar in operation to plunger capture members 26a and 26b) to attach to piston flange 44. As clear to one skilled in the art, many other types of cooperating connection mechanisms can be used to connect an intermediate drive member between an injector drive member and a syringe plunger. Forward section 144 of piston extension 140 can, for example, rotate relative to rear section 148 via bearings 152a and 152b. As illustrated in FIG. 2A an outer housing 105 (illustrated in dashed lines) can encompass the above-described adapter components.

In the embodiment of FIGS. 2A and 2B, motor 200 is attached to adapter 100 via an attachment member or plate 230. The direction and angular velocity of adapter section 110 and, thereby, syringe 20 can, for example, be controlled through use of an encoder or other controller 240 in operative connection with motor 200. The rotation can, for example, be made continuous in a single direction or the rotational direction can be oscillatory. In addition, the rate, duration and/or dwell period of activation of adapter 100 can be controlled in coordination with the operation of the injection (for example, it may be advantageous to re-suspend the contrast agent only just before and/or during an injection to enhance agent life. Moreover, the motion of adapter 100 can also be changed as a function of the position of plunger 25 within syringe 20. The position of plunger 25 within syringe 20 can be determined by various means known in the art including, for example, via a counter or encoder 48 in operative connection with piston 40. For example, more vigorous agitation can be effected when plunger 25 is in a rearward position and the volume of injection fluid within syringe 20 is greater as compared to the case when plunger 25 is in a more forward position. Controller 240 can, for example, be in operative communication with the data input system(s) 14 of injector 10 as well as the other control system(s) 16 of injector 10 as illustrated schematically in FIG. 2A.

Moreover, additional types of agitating motion, such as vibration, can be imparted by adapter 100 to syringe 20. For example, a vibrating mechanism 170 (see FIG. 2B) can be in operative connection with syringe interface 160, which can be attached to adapter section 110 in a manner (as known in the art) to facilitate vibration of syringe interface 160.

Adapter 100 and other adapters of the present invention are readily compatible with pressure sensing mechanisms present on current injector systems or can add pressure sensing capability to such injection systems so that, for example, pressure on micro-bubble contrast agents can be monitored and controlled during injection. In the embodiment of FIGS. 2A and 2B, pressure monitoring is effected via a load cell or sensor 260 placed between 40 piston and piston extension 140 of adapter 100. The force on load cell 260 corresponds to the pressure within syringe 20. A pressure sensing mechanism such as described in U.S. Pat. No. 5,808,203, the disclosure of which is incorporated herein by reference, can also be used in the adapters of the present invention.

Adapter 100 and other adapters of the present invention are also readily compatible with detection mechanism(s) on injector systems (such as via the cooperation of one or more injector sensors 270 with corresponding indicators) to sense when the adapter is attached to the injector system so that, for example, the operator can be notified/assured of correct attachment or so that injector configuration is set for use with an adapter (for example, the injector system, once detecting the presence of the adapter, can prompt the operator for agitation settings.) Detection mechanisms or sensors suitable for use in the present invention are described, for example, in U.S. Pat. Nos. 5,383,858 and 5,944,694, the disclosures of which are hereby incorporated by reference. Likewise, adapter 100 and other adapters of the present invention can be provided with one or more sensors 280 to determine, for example, syringe connection and syringe configuration. As described in U.S. Provisional Application Serial No. 60/317,255, the disclosure of which is incorporated herein by reference, adapter 100 and other adapters of the present invention can include a syringe interface suitable to connect to syringes of different size.

In addition to the control of injection parameters, the operation (for example, the rate, duration and/or dwell period of activation as described above) of adapter 100 can be controlled in coordination with the syringe configuration as detected by sensor(s) 280 or other sensing mechanism(s). As used herein, the term "syringe configuration" is used to encompass all information about a particular syringe, including, but not limited to, information about the mechanical properties of a syringe (for example, material, length, diameter and/or volume) as well as information about the contents of the syringe (for example, fluid volume and/or composition). For example, it may be desirable to adjust agitation motion of adapter 100 (and other adapters of the present invention) as a function of syringe length, diameter and/or volume. Moreover, the identity/composition of a multi-component fluid or fluids within a syringe (which can, for example, be part of the detected syringe configuration in the case of a prefilled syringe) can also affect the operation of adapter 100. For example, depending upon factors such as bubble size and/or fluid viscosity, more or less agitation may be desirable for particular ultrasound contrast media. The adjustments made in the control of adapter 100 and other adapters of the present invention as a result of detected syringe configuration can be effected manually or automatically, for example, by preprogramming the control of adapter 100 for various syringe configurations. For example, a memory 17 in communication with a processing unit 19 in control system 16 can store one or more programs for controlled agitation for a variety of syringe configurations/injection fluid compositions.

A comparison of FIGS. 2C and 2D illustrates the effectiveness of adapter 100. In the experimental setup used in collecting the data of FIGS. 2C and 2D, a spectral Doppler flow phantom was used to measure the relative return signal from diluted micro-bubbles flowing past a 4 MHz probe. The contrast agent used was LEVOVIST (available from Schering AG of Berlin, Germany) mixed at a concentration of 200 mg/ml, and was injected/delivered at a flow rate of 12 mL/min. In comparing FIGS. 2C and 2D, it is seen that signal intensity remains relatively constant with agitation whereas signal intensity varies substantially without agitation.

Figure 2E:
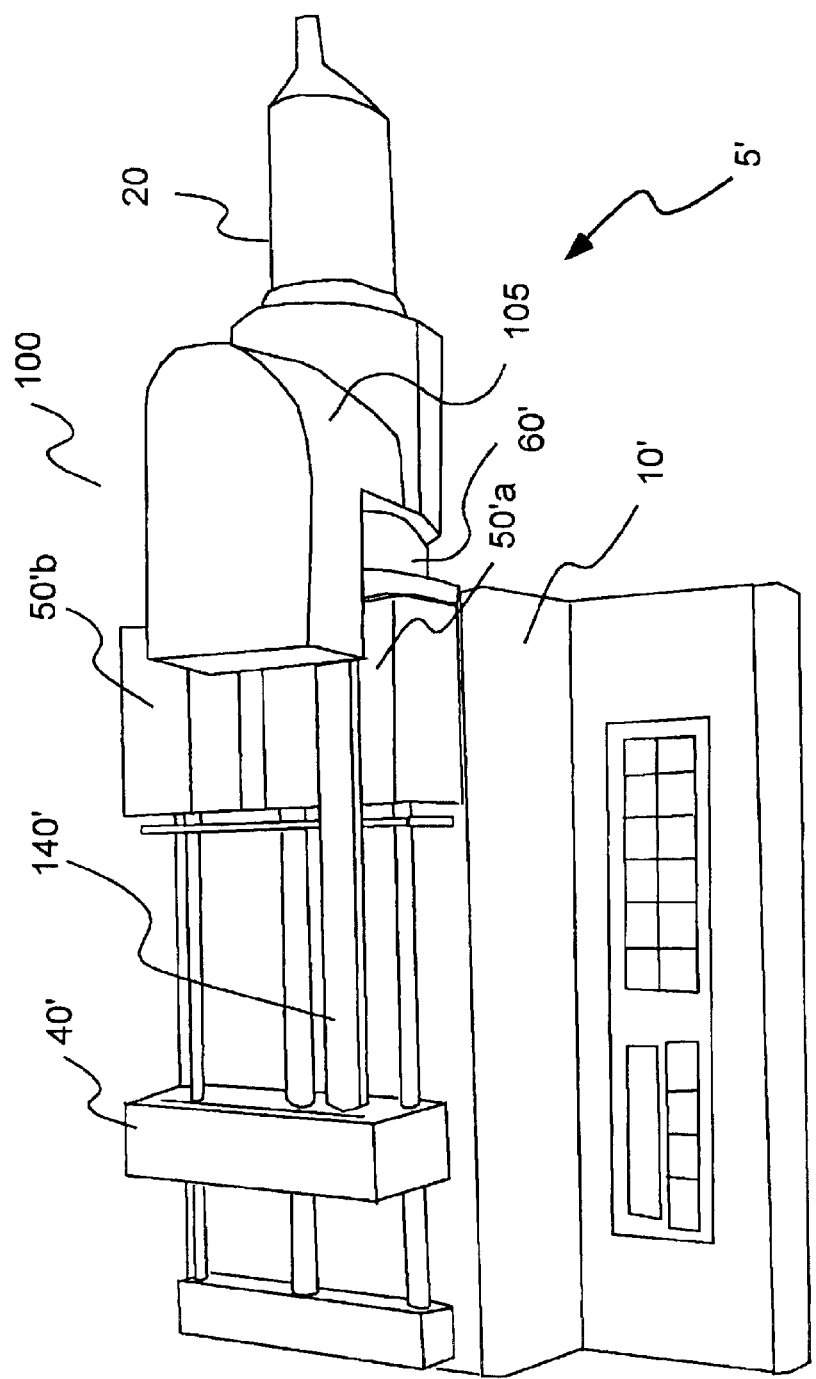
FIG. 2E illustrates the use of an adapter of the type of FIG. 2A on a powered injector used in the experiments of FIGS. 2C and 2D.

FIG. 2E illustrates powered injector system 5' used in the experiments of FIGS. 2C and 2D. Powered injector 10' is a commercially available Harvard Apparatus syringe pump. Powered injector 5' includes a drive member 40' which cooperates with a plunger extension of a manually operated syringe (not shown) to inject a fluid as known in the art. Such manually operated syringes can be seated in syringe seatings 50'a and 50'b.

In the embodiment of FIG. 2E, an interface 60', substantially identical to syringe interface 60 of injector system 5 was first attached to a forward section of injector 10'. Interface 60' facilitated removable attachment of adapter 100 to injector 10' without modification of adapter 100. However, adapter 100 can be readily modified to attach directly to injector 10'. An intermediate drive member 140' was used to translate the motion of drive member 40' to syringe plunger 25 (not shown in FIG. 2E).

FIGS. 3A and 3B illustrate another embodiment of an adapter 300 of the present invention that is operable to rotate syringe 20 about an axis A' that is perpendicular to the longitudinal axis A of syringe 20 (or collinear with the radial direction with respect to syringe 20'). Adapter 300 includes an outer rotating adapter section 310 including a groove or slot 312 therein in which rotating belt 220 is seated as described above for housing 110. Adapter 300 can, for example, be attached to syringe interface 60 of an injector such as injector 10 via flanges 322a and 322b on a rearward portion of adapter 300. Housing 310 is in operative connection with a syringe support 330 to which syringe 20' can be mounted in any manner know in the art (for example, through securing rear syringe flanges 22a' and 22b'). Syringe support 330 rotates with adapter section 310 to rotate syringe 20' and the contents thereof. Adapter section 310 rotates about an inner stationary adapter section 320 via, for example, bearings as known in the art.

Linear reciprocal motion is imparted to syringe plunger 25 from piston 40 via an intermediate drive member or mechanism including two lateral gear racks 360a and 360b. Gear racks 360a and 360b are in operative connection with and rotate with the same direction and angular velocity as adapter section 310 and syringe support 330. Gear racks 360a and 360b are in operative connection with piston 40 via an intermediate connector 362 that does not rotate. Connector 362 can, for example, connect to piston flange 44 via L-shaped capture members 364a and 364b as described above. Gear racks 360a and 360b can, for example, rotate relative to connector 362 via bearings 366 as known in the art. Lateral gear racks 360a and 360b are in operative connection with a pinion gears 370a and 370b which are in operative connection with longitudinal gear racks 380a and 380b. Pinion gears 370a and 370b translate the lateral motion of piston 40 and lateral gear racks 360a and 360b, respectively, to longitudinal motion of longitudinal gear racks 380a and 380b which are movably attached to syringe support 330.

In the embodiment of FIGS. 3A and 3B, longitudinal gear racks 380a and 380b are connected via a bridging or cross member 382. A seating 384 is formed in cross member 382 to removably seat a rear flange 29' formed on a plunger extension 27' of plunger 25'. Syringe support 330 preferably includes seatings 332a and 332b which cooperate with flanges 22a' and 22b' of syringe 20' to removably seat syringe flanges 22a' and 22b', respectively. Advancing piston 40 in the direction of adapter 300 thus causes forward motion of lateral gear racks 360a and 360b and clockwise rotation of pinion gears 370a and 370b about axle 372. This clockwise motion of pinion gears 370a and 370b cause longitudinal rack gears 380a and 380b to move forward with respect to the orientation of syringe 20'. Seatings 332a and 332b hold the barrel of syringe 20' motionless with respect to the forward motion of longitudinal rack gears 380a and 380b. However, the cooperation of seating 384 of bridge member 382 and plunger extension flange 28' causes plunger 25 to move forward with the forward motion of longitudinal rack gears 380a and 380b, thereby advancing plunger 25 within the barrel of syringe 20. Reverse motion of piston 40 is similarly translated into rearward motion of plunger 25' relative to the barrel of syringe 20'. The position of plunger 25 is thus controlled by piston 40 while adapter 300 rotates syringe 20' about axis A' as represented by the arrow R in FIG. 3B. The direction and speed of rotation about axis A' can, for example, be controlled via encoder 240 in operative connection with motor 200 as described above. Once again, additional types of agitating motion, such as axial rotation and vibration, can be provided by adapter 300 via mechanisms disclosed herein and other mechanisms known in the art.

Figure 4A:
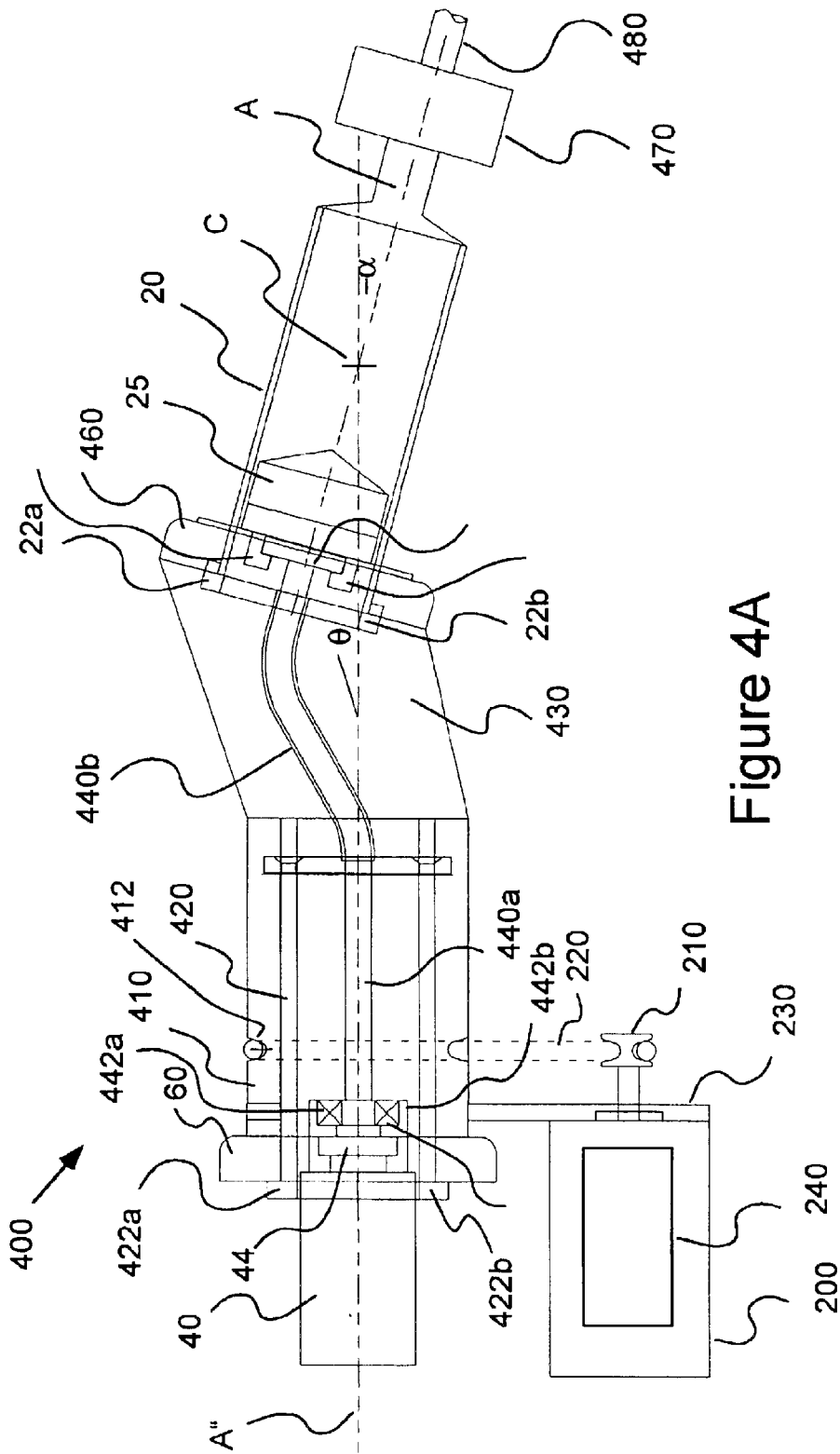
FIG. 4A illustrates a cutaway view of another embodiment of an adapter of the present invention in which the syringe (illustrated as transparent) is orbited.
Figure 4B:
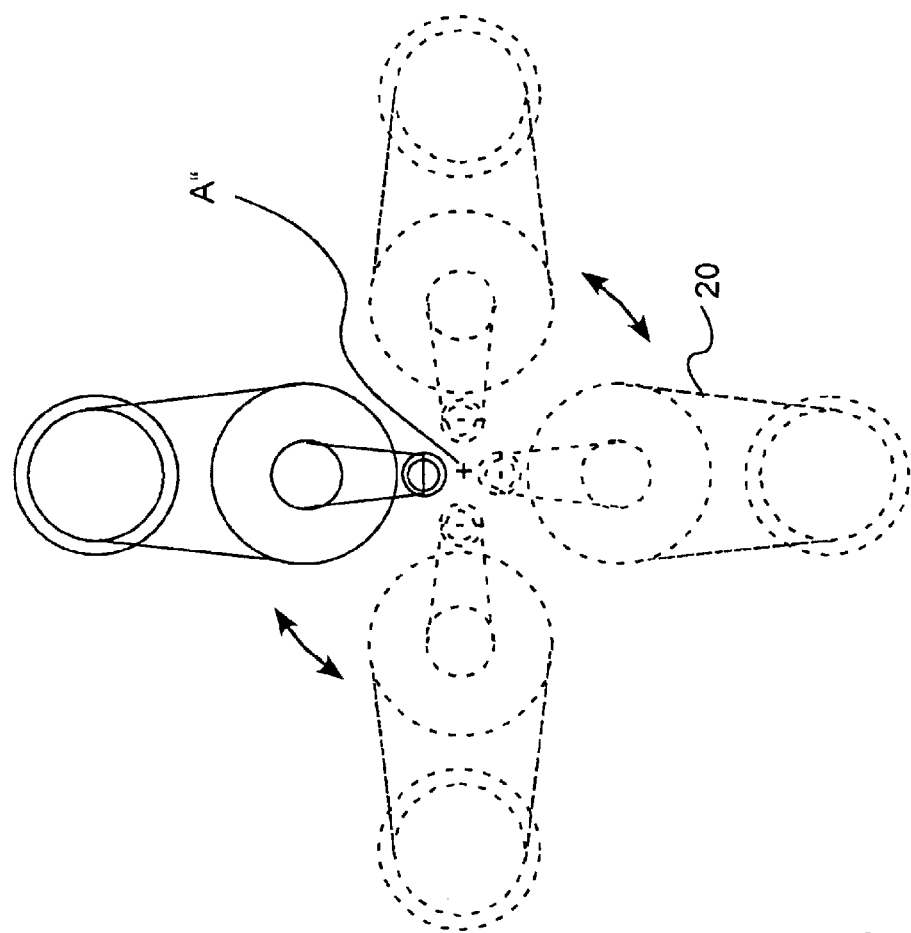
FIG. 4B illustrates the manner in which the syringe can be orbited using an adapter as illustrated in FIG. 4A.

FIGS. 4A and 4B illustrate another embodiment of an adapter 400 of the present invention in operative connection with syringe interface 60 of injector 10. Adapter 400 includes an outer rotating adapter section 410 including a groove or slot 412 therein in which a rotating belt 220 is seated as described above for adapter sections 110 and 310. Adapter section 410 rotates about an inner stationary adapter section 420 via, for example, bearings as known in the art. Adapter 400 can, for example, be attached to an injector such as injector 10 via flanges 422a and 422b on a rearward portion of adapter 400 as described above. Adapter section 410 is in operative connection with a syringe support 430 having a syringe interface 460 to which syringe 20 can be mounted in any manner know in the art (for example, through securing rear syringe flanges 22a and 22b as described above). As illustrate in FIG. 4, syringe support 430 is angled at an angle θ with respect to axis A" of adapter section 410 of adapter 400. Syringe 20 is attached to syringe support 430 at an angle-α. Syringe support 430 rotates with adapter section 410 to cause syringe 20 and the contents thereof to orbit about axis A" as illustrated in FIG. 4B. For clarity, the orbit illustrated in FIG. 4B has been expanded or exaggerated beyond that of syringe 20 attached to the adapter of FIG. 4A. In the embodiment of FIG. 4A, point C on longitudinal axis A of syringe 20 remain generally stationary during the orbit of syringe 20. The angled connections between syringe support 430 and adapter section 410 and between syringe 20 and syringe support 430 can provide a combination of mixing in two axes for additional mixing. The angles of attachment affect the degree of longitudinal mixing and axial mixing and can be varied to give different results, thereby providing the potential to optimize mixing.

In the case of the adapters of the present invention, movement (for example, rotation and/or orbiting) of the syringe can cause problems (for example, entanglement) with tubing and other fluid path elements connected to the syringe. As illustrated in FIG. 4A, a connector 470 can be provided to prevent at least a portion of the motion of syringe 20 from being translated to tubing or other fluid path element 480 connected to syringe 20. In the case of rotation of syringe 20 about its longitudinal axis, connector 470 can, for example, be a swivel nut type connector as known in the medical arts.

Because syringe support 430 orbits about axis A" a flexible piston extension 440A is preferably used to operatively connect piston 40 to plunger 25. Piston extension 440A can, for example, be a flexible push-pull cable. A generally rigid guide 440b can be provided to guide the motion of piston extension 440a therein.

Figure 5:
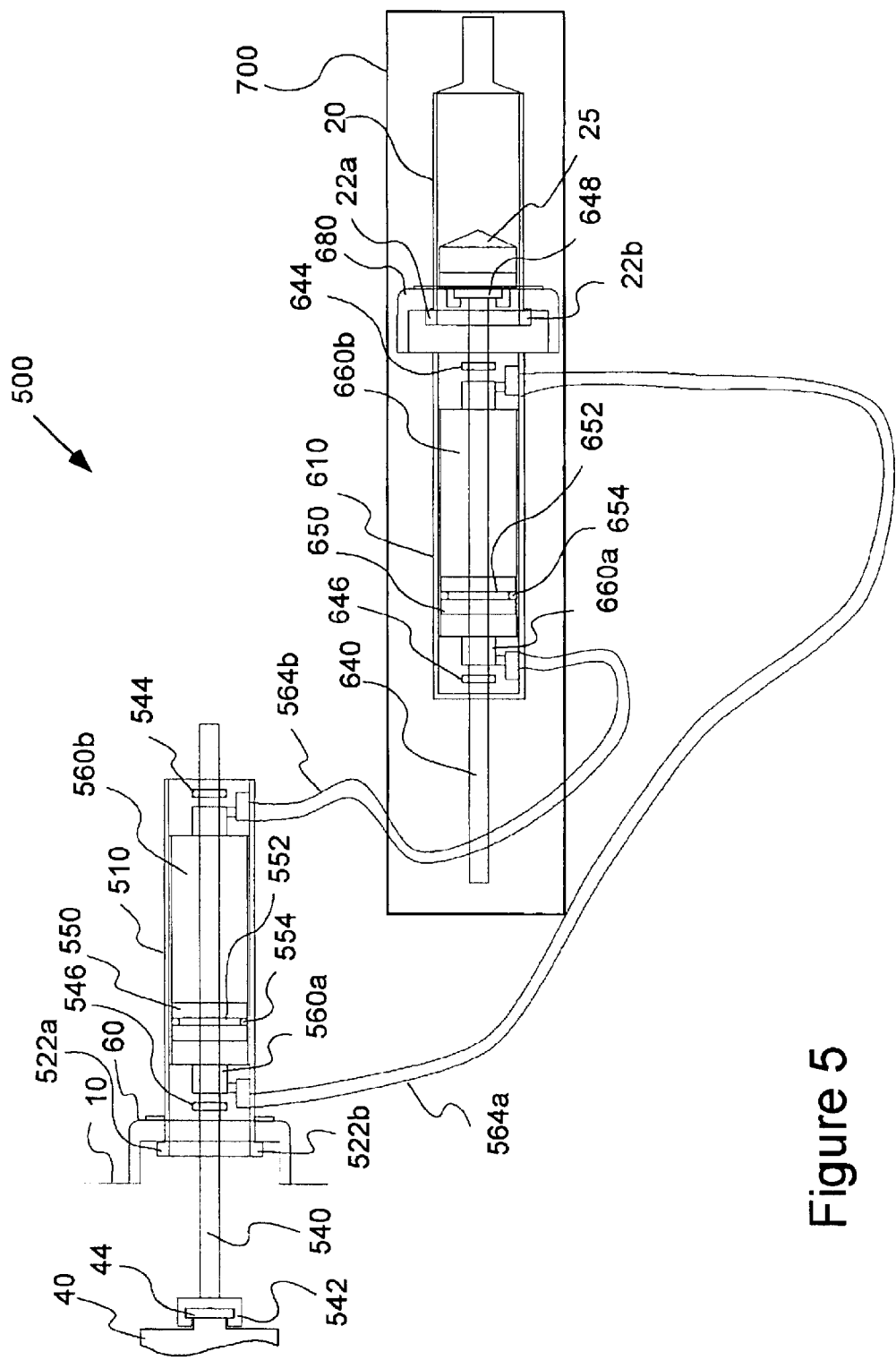
FIG. 5 illustrates a cutaway view of an embodiment of an adapter of the present invention in which the reciprocating motion of the drive member of a powered injector is use to power a hydraulic drive mechanism so that a syringe can be positioned remote from the injector for connection to an agitating mechanism.

FIG. 5 illustrates another embodiment of an adapter 500 of the present invention in which the syringe is flexibly attached to an injector such as powered injector 10. In the representative embodiment of FIG. 5, adapter 500 includes two hydraulic chambers or cylinders 510 and 610. Cylinder 510 is operatively attached to syringe interface 60 of injector 10 via flanges 522a and 522b as described above. A drive member 540 of cylinder 510 is operatively connected to flange 44 of piston 40 via a connector 542. Drive member 540 is operatively connected to a seal member 550 that is slidably positioned within cylinder 510 such that movement of piston 40 is translated to movement of seal member 550. Seal member 550 can, for example, be a metallic or other type of plug member having a groove 552 in which a sealing O-ring 554 is seated. A first fluid-filled chamber 560a is positioned to the rear of seal member 550, while a second fluid-filled chamber is positioned to the front of seal member 550. The respective volumes of fluid-filled chambers 560a and 560b are determined by the position of seal member 550. Cylinder 510 further includes seals such as O-rings 544 and 546 to create a seal around drive member 540.

Cylinder 610 includes a drive member 640 that is in operative connection with syringe plunger 25 via a drive member flange 644. Drive member 640 is also in operative connection with a seal member 650 that is slidably disposed within cylinder 610. As described above for seal member 550, seal member 650 can, for example, be a plug member having a groove 652 in which a sealing O-ring 654 is seated. A first fluid filled chamber 660a is positioned to the rear of seal member 650, while a second fluid-filled chamber is positioned to the front of seal member 650. The respective volumes of fluid-filled chambers 660a and 660b are thus determined by the position of seal member 650. Cylinder 610 further includes seals such as O-rings 644 and 646 to create a seal around drive member 640.

Cylinder 650 can, for example, include a syringe interface 680 to which syringe 20 is attached via flanges 22a and 22b as described above. Drive member 640 is in operative connection with syringe plunger 25 via, for example, flange 644.

Chamber 560a is in fluid connection with chamber 660b via a flexible connecting line 564a. Chamber 560b is in fluid connection with chamber 66a via a flexible connecting line 546b. Forward motion of piston 40 causes forward motion of seal member 550, thereby reducing the volume of chamber 560b and causing fluid (which is generally incompressible) to pass through line 564b and into chamber 660a of cylinder 610. The entry of fluid into chamber 660a causes sealing member 650 to move forward within cylinder 610 and causes fluid from chamber 660b to pass through line 564a into chamber 560a of cylinder 510. The forward motion of sealing member 650 results in forward motion of drive member 640 and, thereby, forward motion of plunger 25.

Similarly, rearward motion of piston 40 causes rearward motion of seal member 550, thereby increasing the volume of chamber 560a and causing fluid to pass through line 564a and into chamber 660b of cylinder 610. The entry of fluid into chamber 660b causes sealing member 650 to move rearward within cylinder 610 and causes fluid from chamber 660a to pass through line 564b into chamber 560b of cylinder 510. The rearward motion of sealing member 650 results in rearward motion of drive member 640 and, thereby, rearward motion of plunger 25. In the above manner, motion of piston 40 of powered injector 10 is translated into motion of syringe plunger 25.

Operative connection of syringe 20 to powered injector 10 via flexible lines 564a and 564b facilitate imparting agitating motion to syringe 20 to agitate an injection fluid therein. In the embodiment of FIG. 5, syringe 20 and cylinder 610 are operatively connected to an agitation mechanism 700 which can impart virtually any type of motion to syringe 20 (for example, axial rotation, longitudinal rotation, orbiting motion and/or vibration) in a manner or manners described herein or as otherwise known in the art.

Although the present invention has been described in detail in connection with the above embodiments and/or examples, it is to be understood that such detail is solely for that purpose and that variations can be made by those skilled in the art without departing from the spirit of the invention except as it may be limited by the following claims.

What is claimed is:

1. An adapter for use with a powered injector to impart agitating motion to a syringe which is connectable to the powered injector, the powered injector having a drive member to impart motion to a plunger slidably disposed within the syringe; the adapter comprising:

an injector attachment mechanism to attach the adapter to the powered injector;

a syringe interface to attach the syringe to the adapter;

an intermediate drive member including a drive attachment to attach the intermediate drive member to the drive member of the powered injector and a plunger attachment member to attach the intermediate drive member to the syringe plunger; and at least one powered agitator to provide agitating motion the syringe interface.

2. The adapter of claim 1 wherein the powered agitator rotates the syringe interface to rotate the syringe about its longitudinal axis.

3. The adapter of claim 1 wherein the powered agitator rotates the syringe interface to rotate the syringe about an axis perpendicular to its longitudinal axis.

4. The adapter of claim 3 wherein the agitator includes a motor and a drive belt in operative connection with the syringe interface.

5. The adapter of claim 1 wherein the powered agitator orbits the syringe interface about an orbital axis to orbit the syringe about the orbital axis.

6. The adapter of claim 5 wherein the agitator includes a motor and a drive belt in operative connection with the syringe interface.

7. The adapter of claim 1 wherein the intermediate drive member includes a flexible connector.

8. The adapter of claim 7 wherein the adapter includes a first hydraulic cylinder to which the injector attachment mechanism is connected, the first hydraulic cylinder being in fluid connection via at least one flexible line with a second hydraulic cylinder to which the syringe interface is connected.

9. The adapter of claim 7 wherein the agitator includes a motor and a drive belt in operative connection with the syringe interface.

10. The adapter of claim 9 wherein the adapter includes a first section to which the injector attachment mechanism is connected and a second section to which the syringe interface is connected, the second section being connected to the first section at an angle, the drive belt being in operative connection with the first section to rotate the first section about its longitudinal axis.

11. The adapter of claim 1 further including a syringe configuration sensing mechanism.

12. The adapter of claim 11 wherein the syringe configuration sensing mechanism is in operative connection with the powered agitator to effect control of the powered agitator as a function of syringe configuration.

13. A powered injector system comprising:
   a powered injector including a drive member to impart motion to a syringe plunger slidably disposed in a syringe that is connectable to the powered injector; and
   an adapter for use with the powered injector to impart agitating motion to a syringe which is connectable to the powered injector; the adapter including:
      an injector attachment mechanism to attach the adapter to the powered injector;
      a syringe interface to attach the syringe to the adapter;
      an intermediate drive member including a drive attachment to attach the intermediate drive member to the drive member of the powered injector and a plunger attachment member to attach the intermediate drive member to the syringe plunger; and
      at least one powered agitator to provide agitating motion the syringe interface.

14. A method of providing a powered injector system with the capability to impart the agitating motion to a syringe, which is connectable to a powered injector of the powered injector system, the method comprising the step of:
   attaching an adapter the powered injector, the adapter including:
      an injector attachment mechanism to attach the adapter to the powered injector;
      a syringe interface to attach the syringe to the adapter;
      an intermediate drive member including a drive attachment to attach the intermediate drive member to the drive member of the powered injector and a plunger attachment member to attach the intermediate drive member to the syringe plunger; and
      at least one powered agitator to provide agitating motion the syringe interface.

15. The method of claim 14 further including the steps of:
   attaching a syringe to the syringe interface; and
   activating the powered agitator.

16. The method of claim 14 further including the step of sensing the syringe configuration of a syringe attached to the syringe interface.

17. The method of claim 16 further including the step of controlling the powered agitator in correspondence with the sensed syringe configuration.

* * * * *